United States Patent [19]

Helioff et al.

[11] Patent Number: 5,024,779
[45] Date of Patent: Jun. 18, 1991

[54] CREAMY NAIL POLISH REMOVER CONTAINING HYDROLYZED AND NEUTRALIZED MALEIC ANHYDRIDE $C_1$–$C_4$ ALKYL VINYL ETHER COPOLYMER

[75] Inventors: Michael W. Helioff, Westfield; Mohammed Tazi, Wayne, both of N.J.; Yoon T. Kwak, Brooklyn, N.Y.; Robert B. Login, Oakland, N.J.

[73] Assignee: GAF Chemicals Corporation, Wayne, N.J.

[21] Appl. No.: 578,173

[22] Filed: Sep. 6, 1990

[51] Int. Cl.$^5$ ................................................ C11D 7/00
[52] U.S. Cl. .............................. 252/162; 252/DIG. 8; 252/174.23; 252/170; 252/174.24; 134/38
[58] Field of Search ................... 252/DIG. 8, 174.23, 252/162, 170, 174.24; 134/38

[56] References Cited

U.S. PATENT DOCUMENTS 4,197,212 4/1980 Minton et al. ................. 252/DIG. 8
4,781,916 11/1988 Papaphilippou ............... 252/DIG. 8
4,804,486 2/1989 Day ............................... 252/DIG. 8

*Primary Examiner*—Paul Lieberman
*Assistant Examiner*—Cynthia Leslie
*Attorney, Agent, or Firm*—Walter Katz; Marilyn J. Maue; Joshua J. Ward

[57] ABSTRACT

What is disclosed herein is a nail polish remover composition having a cream-like consistency, and, in use, leaves a thin, bufferable coating on the nail which does not yellow, peel or crack, is non-toxic, and which can be removed easily with soap and water. The active components are (a) about 50 to 95% by weight of a solvent to remove nail polish from the nail; and (b) about 0.25–3.0% by weight of a hydrolyzed and neutralized crosslinked maleic anhydride-$C_1$–$C_4$ alkyl vinyl ether copolymer, which is neutralized with about 0.2 to 2.4% by weight of a neutralizing agent.

8 Claims, No Drawings

CREAMY NAIL POLISH REMOVER CONTAINING HYDROLYZED AND NEUTRALIZED MALEIC ANHYDRIDE $C_1$–$C_4$ ALKYL VINYL ETHER COPOLYMER

BACKGROUND OF THE INVENTION

1. Field of the Invention

This invention relates to a nail polish remover composition, and more particularly, to a composition having a cream-like consistency.

2. Description of the Prior Art

Commonly nail polish is an organic resin in a carrier liquid in which the resin is deposited on a fingernail for decorative purposes For various reasons it may be desirable to remove the nail polish from the fingernail. Chemically nail polish may be removed by applying a solvent, preferably in a carrier, to the polished nail for dissolving the resin therein for subsequent removal, as by wiping.

Present removers are generally a clear, free-flowing liquid which may include a water carrier and an acetone and/or ethyl acetate solvent in appropriate proportions and various function-specific additives. This system presents a problem in that both acetone and ethyl acetate have high vapor pressures at room temperature and low flash points. These properties make the removers volatile and inhibit use in a heated area, such as a kitchen or near a heat source.

Furthermore, many removers are a clear liquid, but it is believed that a cream-like consistency cosmetic-like material would be more esthetically and functionally desirable. This is particularly true if the remover employs a high flash point solvent.

The prior art in this field is represented by the following U.S. Pat. Nos. 2,197,630; 2,268,642; 2,286,687; 2,351,195; 4,032,464; 4,197,212; 4,412,027; 4,485,037; 4,804,486; and related patents cited therein.

It is therefore an object of this invention to provide a nail polish remover having a cream-like consistency and a cosmetic-like appearance.

Another object of the invention is to provide a creamy nail polish remover composition which is controllable in use, and particularly, doesn't run, can be applied to spot areas of the nail for efficient removal of nail polish, and which leaves a thin, bufferable coating on the nail which is non-toxic, doesn't yellow, peel or crack, does not show a whiting effect, and can be removed easily with soap and water.

Still another object herein is to provide such a composition whose consistency can be predetermined from a thin to relatively stiff composition, as desired, and preferably is present as a soft, easily applied, consumer acceptable, convenience-oriented product.

These and other objects and features of the invention will be made apparent from the following description thereof

SUMMARY OF THE INVENTION

What is disclosed herein is a nail polish remover composition which exhibits a cream-like consistency, and which leaves a thin, bufferable coating on the nail after use which does not yellow, peel or crack, is non-toxic, and which can be removed easily when desired by application of soap and water.

The nail polish remover composition of the invention includes a suitable solvent such as acetone, which is rendered cream-like by the presence of a hydrolyzed and neutralized crosslinked maleic anhydride-$C_1$–$C_4$ alkyl vinyl ether copolymer in an amount effective to form a gel, usually about 0.25 to 3.0% by weight of the compostiion.

The neutralizing agent in the composition maintains the copolymer in the gelled state. A suitable neutralizer is sold commercially under the trademark Ethomeen C-25 by Akzo Chemie, which is a polyethylene glycol cocamine.

A preferred component in the composition is a humectant such as propylene glycol which provides a smooth feel to the user upon application. Water is used therein to balance the composition to 100 percent and to provide an aqueous-acetone solvent base.

The composition herein preferably is soft upon application, and has a viscosity measured by a Brookfield viscometer of about 10,000 to 50,000 cps.

DETAILED DESCRIPTION OF THE INVENTION

1. Active Components

The nail polish remover composition described hereinafter includes a number of components, only some of which are considered active in the remover. These active components can be categorized as (a) the solvent; and (b) the hydrolyzed and neutralized copolymer gel of maleic anhydride and a $C_1$–$C_4$ alkyl vinyl ether.

(a) Solvent

The solvent used herein is particularly effective for removing nail polish. Generally the solvent is employed in an amount of about 50 to 95% by weight of the composition, preferably about 60 to 85%, and most preferably about 80%. Suitable solvents include acetone, methyl ethyl ketone, ethyl acetate, butyrolactone and mixtures thereof. Acetone is preferred.

(b) Hydrolyzed and Neutralized Crosslinked Copolymer Gel of Maleic Anhydride and a $C_1$–$C_4$ Alkyl Vinyl Ether The hydrolyzed and neutralized, crosslinked maleic anhydride-$C_1$–$C_4$ alkyl vinyl ether copolymer gel is prepared by polymerizing maleic anhydride, a $C_1$–$C_4$ alkyl vinyl ether and a crosslinking agent in the presence of a suitable free radical initiator.

A solvent may be used for the polymerization, such as benzene, toluene, xylene, acetone, methyl ethyl ketone and methylene chloride. However, it is preferred to use a solvent mixture of a carboxylic acid ester and a saturated cycloaliphatic hydrocarbon. A particularly preferred solvent system is a mixture of ethyl acetate and cyclohexane, preferably in the weight ratio of about 35 to 55% ethyl acetate to about 45 to 65% cyclohexane.

In this solvent system, the crosslinked copolymer product is provided in pumpable slurry form, from which dry, fine, white powders can be obtained easily. The copolymer powders then can be readily hydrolyzed to clear gels of high viscosities with good stability and excellent salt tolerance.

The amount of crosslinking agent used in polymerization generally varies from about 1 to about 5 mole percent based on the monovinyl alkyl ether. Examples of suitable crosslinking agents include diunsaturated compounds such as the divinyl ethers of an aliphatic diol, e.g. the divinyl ethers of 1,2-ethanediol; 1,3-propanediol; 1,4-butanediol, 1,5-pentanediol; 1,6-hexanediol; 1,7-heptanediol; 1,8-octanediol; 1,9-nonanediol;

1,10-decanediol; 1,11-undecanediol; and 1,12-dodecanediol, as well as the divinyl ethers of diethylene glycol, triethylene glycol, tetraethylene glycol, pentaethylene glycol; hexaethylene glycol, heptaethylene glycol, octaethylene glycol, nonaethylene glycol, decaethylene glycol and further polyalkylene glycols up to a molecular weight of about 5900. Other suitable cross-linking agents include 1,7-octadiene, 1,9-decadiene, divinylbenzene, N,N'-bis-methylene acrylamide, acrylates such as polyethylene glycol diacrylate, trimethylolpropane triacrylate, propylene glycol diacrylate, polyhydric alcohols esterified once or twice with acrylic acid triallylamine, tetraallylethylenediamine, diallyl phthalate, and the like.

The polymerization is carried out conveniently by preparing the mixed solvent solution of the monomers and adding a catalytic amount (generally from 0.001 to 1.0%) of an organic free radical-generating initiator. The resulting solution then is mixed thoroughly and heated sufficiently so that the polymerization reaction takes place. At the completion of the polymerization reaction, the precipitated interpolymer slurry is pumped from the reactor and the copolymer is isolated by any suitable means such as by filtration or distillation of solvent, washed with fresh solvent and vacuum dried.

Suitable organic free radical-generating initiators for use in the polymerization include azobisisobutyronitrile, benzoyl peroxide, lauroyl peroxide, caprylyl peroxide, acetyl peroxide, acetyl benzoyl peroxide, di-tert-butyl peroxide, t-butyl peroxypivalate, azobis(2,4-dimethylvaleronitrile) and the like. Mixtures of such catalysts are also suitable in the process of making these polymers.

The polymerization is carried out at a temperature within the range of from 50° to 100° C., particularly about 60°-80° C.

After obtaining the dry powder copolymer, the anhydride groups therein are hydrolyzed and neutralized in aqueous basic solution at a suitable temperature, e.g. about 35°-40° C. Suitably, a 0.25 to 3.0%, preferably 1 25% by weight copolymer is dissolved in about 5-15 g. of water and about 0.2 to 2.4 g., preferably about 1.0 g. of Ethomeen C-25. The resultant pH of the clear hydrolyzed and neutralized copolymer is about 5-7.

The clear, hydrolyzed and neutralized copolymer in acetone is the gelled base of the composition of the invention. The viscosity of the composition is determined at 25° C. with a RTV Brookfield viscometer spindle TD type at 10 rpm. Suitable viscosities range from about 10,000 to about 50,000 cps, and, preferably about 12,000 to 24,000. A viscosity of about 18,000 is most preferred for the nail polish remover compositions of the invention.

Since it is necessary to provide the copolymer in neutralized form in the composition, in order to maintain a gelled state, a neutralizing agent is included in the composition. Preferred neutralizing agents include organic amines, e.g. Ethomeen C-25, which is a polyethylene glycol-15 cocamine, or PEG-15 cocamine. Ethamines which have PEG-2, 5, or 10 components also may be used, as well as triethylamine, triamylamine, triethanolamine, 2-amino-2-methyl-1-propanol (AMP) and the like.

2. Preferred Components

Water

Water is preferably included in the composition to reduce the volatility of acetone without substantially affecting its effective action against nail polish. Preferably, up to about 25% by weight water is included in the composition, most preferably about 5-15%, and optimally about 10%.

Humectant

A humectant may be included in the composition to provide a smoother feel to the user upon application. Suitably, up to about 25% by weight of a humectant may be used, although about 5-15% is preferred, and about 10% is considered an optimum amount. Any suitable humectant may be used for this purpose. Glycols and esters are preferred, including propylene glycols, dipropylene glycols and the like.

| CREAMY NAIL POLISH REMOVER COMPOSITION OF INVENTION | | | |
|---|---|---|---|
| Active | | Percent by Weight | |
| Components | Suitable | Preferred | Optimum |
| Solvent e.g. acetone | 50-95 | 60-85 | 80 |
| Crosslinked Copolymer of Maleic Anhydride and a $C_1$-$C_4$ Alkyl Vinyl Ether | 0.25-3.0 | 0.75-1.75 | 1.25 |
| Neutralizing Agent e.g. Ethomeen C-25 Preferred | 0.20-2.4 | 0.5-1.5 | 1.0 |
| Water | 0-25 | 5-15 | 10 |
| Humectant e.g. propylene glycol | 0-25 | 5-15 | 10 |
| pH | 5.0-7.5 | 6.5-7.5 | 6.8-7.2 |
| Viscosity, cps | 10 to 50,000 | 12,000 to 24,000 | 18,000 |
| Appearance | thin-soft-stiff | soft | soft |

The invention will now be described with reference to the following examples.

EXAMPLE 1

Preparation of Crosslinked Copolymer

A reactor was precharged with a 50:50 weight mixture of ethyl acetate and cyclohexane as a cosolvent composition, and 1,7-octadiene as a crosslinking agent. The reactor was then purged with nitrogen, heated to 58° C., and charged with initiator (Lupersol-11, which is t-butyl peroxypivalate) at a 0.15 to 2% by weight level based on maleic anhydride. Then molten maleic anhydride and methyl vinyl ether were fed separately (or through a common inlet) into the reactor over a 2 to 3 hour period. The reactants were held at that temperature for an additional 1 to 3 hours, then cooled, vented and discharged. The resulting slurry, in which the copolymer product was present at an 18 to 25% solids level, was filtered and dried. Fine white powders of the desired crosslinked copolymer were obtained.

EXAMPLE 2

Preparation of Hydrolyzed and Neutralized Crosslinked Copolymer 1.25 g. of the crosslinked copolymer prepared above was added slowly to 1.0 g. of Ethomeen C-25 and 10.0 ml. of water heated to 35°-40° C. After ½ hour the opaque mixture changed into a clear gel base having a pH of 5-7.

EXAMPLE 3

Formulation and Use of Nail Polish Remover Composition of Invention

In a stainless steel vessel equipped with a mixer the hydrolyzed and neutralized copolymer gel base prepared above was added to 80 g. of acetone, 10 g. of propylene glycol and stirred for 1 hour. The clear, creamy solution had a viscosity of 18,000 cps*. The composition was used for removing nail polish.

*Brookfield viscometer, Model RVT
Spindle TD type rotating at 10 rpm at 25° C.

Upon removal of the nail polish, the water-insoluble copolymer gel of the composition of the invention will form a thin bufferable, moisture impermeable coating on the nail. This coating did not yellow, peel or crack, is non-toxic, and was easily removed by soap and water when desired. No whiting effect was observed.

While the invention has been described with particular reference to certain embodiments thereof, it will be understood that changes and modifications may be made which are within the skill of the art. Accordingly, it is intended to be bound only by the following claims, in which:

What is claimed is:

1. A creamy nail polish remover composition consisting essentially of
   (a) about 50 to 95% by weight of a solvent selected from acetone, methyl ethyl ketone, ethyl acetate and butyrolactone, and mixtures thereof, in an amount effective to remove nail polish from a nail;
   (b) about 0.25 to 3.0% by weight of a hydrolyzed and neutralized crosslinked maleic anhydride-$C_1$-$C_4$ alkyl vinyl ether copolymer gel said copolymer crosslinked with a polyethylenically unsaturated compound;
   (c) about 0.20 to 2.4% by weight of a neutralizing agent;
   (d) about 0-25% by weight of water; and
   (e) about 0-25% by weight of a humectant,
   said composition having a viscosity of about 10,000 to 50,000 cps as measured by a Brookfield viscometer Model RVT at 10 rpm TD spindle at 25° C.

2. A composition according to claim 1 wherein said viscosity is about 18,000 cps.

3. A composition according to claim 1 wherein said copolymer is neutralized with an organic amine.

4. A composition according to claim 1 which includes water.

5. A composition according to claim 1 which includes a humectant.

6. A composition according to claim 1 including:
   (a) about 50 to 95% by weight acetone;
   (b) about 0.25 to 3.0% by weight of hydrolyzed crosslinked maleic anhydride-$C_1$-$C_4$ alkyl vinyl ether copolymer gel;
   (c) about 0.20 to 2.4% by weight of a neutralizing agent;
   (d) about 5 to 25% by weight of water; and
   (e) about 5 to 25% by weight of a humectant.

7. A composition according to claim 5 wherein said neutralizing agent is an organic amine selected from the group consisting of polyethylene glycol cocamine, triethylamine, triamylamine, triethanolamine and 2-amino-2-methyl-1-propanol.

8. A composition comprising:
   (a) about 80% by weight of acetone;
   (b) about 1.25% by weight of a hydrolyzed crosslinked maleic anhydride-$C_1$-$C_4$ alkyl vinyl ether copolymer gel;
   (c) about 0.2 to 2.4% by weight of a neutralizing agent which is a polyethylene glycol cocamine;
   (d) about 10% by weight of water; and
   (e) about 10% by weight of propylene glycol.

* * * * *